United States Patent
Rossen et al.

(10) Patent No.: US 8,618,310 B2
(45) Date of Patent: Dec. 31, 2013

(54) PROCESS FOR PREPARING N-PROTECTED 4-KETOPROLINE DERIVATIVES

(75) Inventors: Kai Rossen, Hanau (DE); Rolf Hoffmann, Hammersbach (DE); Martin Sarich, Alzenau (DE)

(73) Assignee: Evonik Degussa GmbH, Essen (DE)

( * ) Notice: Subject to any disclaimer, the term of this patent is extended or adjusted under 35 U.S.C. 154(b) by 778 days.

(21) Appl. No.: 10/591,340

(22) PCT Filed: Feb. 19, 2005

(86) PCT No.: PCT/EP2005/001750
§ 371 (c)(1),
(2), (4) Date: Aug. 31, 2006

(87) PCT Pub. No.: WO2005/095340
PCT Pub. Date: Oct. 13, 2005

(65) Prior Publication Data
US 2007/0185336 A1   Aug. 9, 2007

(30) Foreign Application Priority Data
Mar. 3, 2004  (DE) .......................... 10 2004 010 943

(51) Int. Cl.
*C07D 207/24*   (2006.01)
(52) U.S. Cl.
USPC ........................................................ 548/541
(58) Field of Classification Search
None
See application file for complete search history.

(56) References Cited

U.S. PATENT DOCUMENTS

| | | | |
|---|---|---|---|
| 4,296,113 | A | 10/1981 | Ondetti |
| 4,470,972 | A | 9/1984 | Gold et al. |
| 5,631,385 | A | 5/1997 | Drauz et al. |
| 6,103,910 | A | 8/2000 | Hertel et al. |

FOREIGN PATENT DOCUMENTS

WO    WO 99/44991    * 3/1999

OTHER PUBLICATIONS

Dormoy et al., Synthesis, 1986, p. 81-82.*
Hacks Chemical Dictionary, Fourth Edition, Julius Grant, 1972, p. 203.*
Merriam-Webster Online Dictionary, copyright 2007-2008.*
Crystallization,Wikipedia, http://en.wikipedia.org/wiki/Crystallization.*
Riley, J. Chem. Soc. Chem. Commun., 1983, 1530-1532.*
Crystallization,Wikipedia, http://en.wikipedia.org/wiki/Crystallization, 2008.*
International Preliminary Examination Report for international application PCT/EP2005/001750, issued Sep. 6, 2006.
International Search Report Dated Jun. 15, 2005.
Baldwin, et al., "Towards a Versatile Synthesis of Kainoids I: Introduction of the C-3 and C-4 Substituents," *Tetrahedron*, vol. 53, No. 14:5233-5254 (1997).
Carlsen, et al., "A Greatly Improved Procedure for Ruthenium Tetraoxide Catalyzed Oxidations of Organic Compounds," *J. Org. Chem.* 46:3936-3938 (1981).
Crawford, "A Practical Synthesis of 7,7,8,8-Tetracyanoguinodimethane," *J. Org. Chem.* 48:1366-1368 (1983).
Kaname, et al., "First Synthesis of Lycoperdic Acid," *Tetrahedron Letters*, vol. 33, No. 52:8103-8104 (1992).
Narukawa, et al., "General and Efficient Synthesis of 2-Alkylcarbapenems: Synthesis of Dethiacarba Analogs of Clinically Useful Carbapenems via Palladium-Catalyzed Cross-Coupling Reaction," *Tetrahedron*, vol. 53, No. 2:539-556 (1997).
Patchett, et al., "Studies on Hydroxyproline," *J. Amer. Chem. Soc.* 79:185-192 (1957).
Qiu, et al., "Practical Synthesis of Boc-Protected *cis*-4-Trifluoromethyl and *cis*-4-Difluoromethyl-L-prolines," *J. Org. Chem.* 67:7162-7164 (2002).
Sain, et al., "A Facile Synthesis of 4-Arylidene-2-Oxazolin-5-Ones by Using *N,N*-Dimethylchlorosulphite Methaniminium Chloride as a Cyclodehydrating Agent," *Chemistry and Industry* 15:499 ( Aug. 1990).
Tamaki, et al., "Synthesis of 4-*cis*-Phenyl-L-proline via Hydrogenolysis," *J. Org. Chem.* 66:3593-3596 (2001).

* cited by examiner

*Primary Examiner* — Sun Jae Loewe
(74) *Attorney, Agent, or Firm* — Law Office of: Michael A. Sanzo, LLC

(57)   ABSTRACT

The present invention is concerned with a process for preparing compounds of the general formula (I). These compounds can preferably be used to prepare bioactive agents. The reaction of the invention starts from the corresponding hydroxy compounds which are oxidized, with Ru catalysis, in a one-phase aqueous system.

(I)

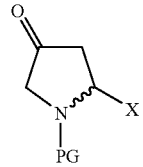

20 Claims, No Drawings

PROCESS FOR PREPARING N-PROTECTED 4-KETOPROLINE DERIVATIVES

CROSS REFERENCE TO RELATED APPLICATIONS

The present application represents U.S. national stage of international application PCT/EP2005/001750, with an international filing date of Feb. 19, 2005 and which was published in English under PCT Article 21(2) on Oct. 13, 2005. The international application claims priority to German application 10 2004 010 943.5, filed on Mar. 3, 2004. The contents of these prior applications are hereby incorporated by reference in their entirety.

The present invention relates to a process for preparing ketoproline derivatives of the general formula (I)

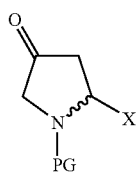

(I)

N-Protected 4-ketoproline derivatives of the general formula I are inter alia important starting compounds for preparing the ACE (angiotensin converting enzyme) inhibitor spirapril[7-(N-(1-(S)-carboethoxy-3-phenyl-propyl)-(S)-alanyl)-1,4-dithia-7-azaspiro[4.4]nonan-8-(S)-carboxylic acid] of the formula II, which is used for treating high blood pressure and cardiovascular disorders (U.S. Pat. No. 4,470,972).

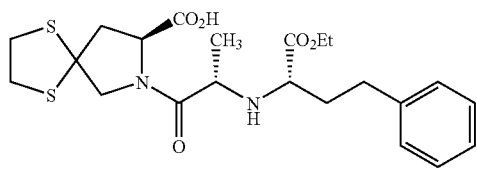

Formula II

4-Ketoproline derivatives are unstable compounds. They can be obtained and stored only under very specific conditions. The instability to bases may be particularly emphasized at this point (Patchett, Arthur A.; Witkop, Bernhard, Journal of the American Chemical Society 1957, 79, 185-92).

DD-A5 283 626 describes a heavy metal-free process for preparing (2S)-N-benzyloxycarbonyl-4-ketoproline which employs a sulfur trioxide-pyridine complex as oxidizing agent. The disadvantage of this process is that the pyridine used is a highly environmentally polluting substance which is highly toxic for humans.

A further heavy metal-free preparation process is described in DE 19524339. In this case, a protected hydroxyproline ester is oxidized with the tempo/NaOCl system in a two-phase mixture. A disadvantage of the described variant is that free hydroxyproline cannot be reacted as acid in this system. Subsequent hydrolysis of the 4-ketoproline ester is impossible because of the described instability to bases. The method described herein is therefore unsuitable for preparing the free acid of 4-ketoproline.

Processes for synthesizing 4-ketoproline derivatives of the general formula I are based inter alia also on the use of heavy metal-containing oxidizing agents such as, for example, various chromium-containing oxidation systems (see U.S. Pat. No. 4,296,113; see also JOC 2001, 66, 3593; JOC 2002, 67, 7162). These processes have the disadvantage that they require additional safety measures while the reaction is carried out, and of an elaborate and costly disposal of heavy metal after completion of the reaction.

Narukawa et al. (Tetrahendron, Vol. 53, No. 2, 1997, pp. 539-556) describe the oxidation of N-protected 4-hydroxyproline in a two-phase mixture of ethyl acetate and water using $RuO_2/NaIO_4$. The yield is reported to be 67% of a white powder.

It can be firmly held overall that $RuO_4$ represents a very strong oxidizing agent. It can be used for the oxidative degradation even of very stable compounds such as PCBs (Beattie, J. K. et al., Pure and Applied Chem. 1990, 62, 1145-6; Creaser C. S. et al., Chemistry & Industry 1988, 15, 499-500).

It was therefore an object of the present invention to indicate a further process for the oxidation of N-protected 4-hydroxyproline derivatives to give the corresponding keto compounds. It was particularly intended that the process be easy to carry out on the industrial scale and be superior to prior art processes with regard to economic and ecological aspects. It was intended to pay particular attention to the fact of a simple process without problems in terms of worker safety.

These objects and others which are not specified in detail but are obvious from the prior art are achieved by a process having the characterizing features of present claim 1. Subclaims dependent on claim 1 relate to preferred embodiments of the process of the invention.

The stated object is achieved in a surprising and, nevertheless, advantageous manner in a process for preparing N-protected 4-ketoproline derivatives of the general formula (I)

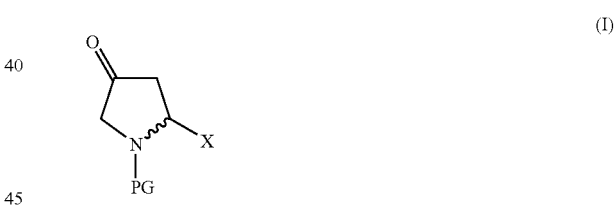

(I)

in which
X is an acid, ester or amide function,
PG is an N-protected group which comprises a carbonyl function and is bonded via this function to the nitrogen, in that this is generated by oxidizing the corresponding 4-hydroxyproline compound with an oxidizing agent in the presence of catalytically active ruthenium compounds in such a way that the oxidation is carried out in an aqueous one-phase system, and the oxidation product (I) is allowed to crystallize out during the addition of the oxidizing agent. As already indicated hereinbefore, compounds of the general formula (I) are unstable compounds able to undergo, especially under alkaline conditions, further transformations (aldol reactions, ring-opening reactions). It has also emerged that the present process functions excellently only if the generated oxidation product (I) crystallizes out where possible immediately after its generation. It thus escapes possible further oxidation in the system. The result is the presence of a very pure reaction product which can be removed from the oxidation system in a simple manner and without complicated extraction processes.

In a preferred embodiment, the present process is carried out at the lowest possible temperatures. It has emerged that it is advantageous to maintain a temperature of ≤30° C., in particular ≤20° C., preferably ≤15° C., during the oxidation.

Oxidizing agents which can be used are also oxidizing agents available to the skilled worker and advantageously employable in the present system. Suitable as such are, in particular, electrochemical or chemical oxidizing agents. Chemical oxidizing agents advantageously employed are hydrogen peroxide or halogen derivatives. Oxidizing agents such as the salts of the hypohalites, halates and perhalates are particularly preferred. Perhalates are very particularly preferred, and of these so-called sodium periodate is extremely preferred.

It is essential in the present process for that resulting oxidation product (I) to be withdrawn after its generation from the system and be protected from further oxidation. This is achieved in the process variant of Narukawa et al. by operating a two-phase system, with the compound to be oxidized and the product being present in the organic phase, and the oxidation system ($RuO_2/NaIO_4$) being present in the aqueous phase. The oxidation consequently takes place only at the interface. In the present case, the oxidation takes place in a one-phase aqueous solvent system. The crystallization out of the oxidation product (I) protects it from further oxidation. It is therefore advantageous for the oxidation product to start to crystallize out as soon as possible after generation. The earlier the onset of crystallization of (I), the fewer further oxidized species produced. These are capable of having an adverse effect on that byproduct spectrum of (I). The procedure for the process on the industrial scale will therefore be to allow the product to crystallize out even during the addition of the oxidizing agent. The skilled worker is familiar with the measures with which he can achieve this. Adjustment of a particular temperature, addition of inorganic or organic substances which have a beneficial influence on the crystallization, and addition of seed crystals, are only some of the available possibilities. In a preferred embodiment of the current process, seed crystals are added after from 30% to 70%, preferably 40% to 60%, particularly preferably 50%, of the oxidizing agent has been added to the reaction mixture. This leads to firstly sufficient oxidized compound (I) being present for the crystallization to be able to start, and secondly insufficient oxidizing agent yet being present for the further oxidation to predominate.

The current process is advantageously carried out in purely aqueous solution. In order to be able to adjust certain solvent properties specifically for the compound to be reacted (acid, ester, amide), it is also possible to add further water-soluble organic solvents to the system as solvents. Suitable solvents of this type are, in particular, those which are inert under the oxidizing conditions. These are, in particular, THF, dioxane, acetonitrile, sulfolanes and acetic acid, dimethyl carbonate.

The procedure for the present process is preferably such that the oxidizing agent, for example sodium (meta)periodate is dissolved in an appropriate amount of water. In parallel, the compound to be oxidized, for example N-protected hydroxyroline, is likewise dissolved in water. After this solution has cooled, an Ru-containing compound (e.g. $RuO_2$ or $RuCl_3$) is added and, finally, while controlling the temperature the periodate solution is metered into the hydroxyproline solution. A suitable Ru-containing compound is one which reacts further to the catalytically active Ru species under the editing conditions. These are in particular Ru salts and complexes, $RuO_2$ and $RuCl_3$ or Ru hydroxides or mixed oxychlorides of ruthenium. After addition of advantageously 50% of the oxidizing agent, for example seed crystals are added to the system to initiate the crystallization. After the total amount of oxidizing agent has been metered into the editing mixture, and after the reaction is complete, the solid can be filtered off and be employed thus and/or after washing with water and/or after drying in the subsequent reaction or further purification. The oxidation products (I) can be purified by processes known to the skilled worker. It may be noted that purification for example by recrystallization from organic solvents is feasible. Isopropyl acetate has proved appropriate in this connection.

Very pure oxidation product (I) is thus obtained in a simple manner and without complicated extraction processes, and has in particular little contamination with further oxidized species. It may be particularly remarkable that stereocenters present in the molecule are evidently unaffected under the reaction conditions. The process proceeds in a highly stereo-conservative manner. It can be carried out both in batch operation and continuously. Concerning continuous oxidation, reference may be made to DE 1037875. The present process can take place with similar advantage in a loop reactor described therein. It is consequently possible, surprisingly, despite the instability of the oxidation products (I) to operate in only one phase in aqueous solution. This was not obviously inferable from the prior art and is particularly advantageous, since the additional extraction step can be omitted in this case.

The starting compounds can be prepared by methods known to the skilled worker (Houben-Weyl, volumes relating to amino acids). Starting compounds taken as preferred are substances of the general formula (III).

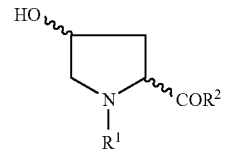

III in which
$R^1$=CO—$R^3$ or fluorenylmethoxycarbonyl,
$R^2$=$NH_2$, $OR^4$,
$R^3$=(H), ($C_1$-$C_8$)-alkyl, phenyl, benzyl, benzyloxy, $NH_2$, $NO_2$-phenyloxy, $NO_2$-benzyloxy, ($C_1$-$C_8$)-alkoxy or phenyloxy,
$R^4$=H, ($C_1$-$C_8$)-alkyl, benzyl, phenyl, $NO_2$-benzyl, $NO_2$-phenyl.

($C_1$-$C_8$)-Alkyl is to be regarded as being methyl, ethyl, n-propyl, isopropyl, n-butyl, isobutyl, sec-butyl, tert-butyl, pentyl, hexyl, heptyl or octyl including all bond isomers. This may be substituted one or more times by halogen.

($C_1$-$C_8$)-Alkoxy is a ($C_1$-$C_8$)-alkyl radical linked via an oxygen atom to the molecule considered.

Suitable halogens (Hal, halogen atom) are fluorine, chlorine, bromine and iodine. Chlorine and bromine is preferred.

PG means an N-protective group. This can be chosen as desired as long as it comprises a carbonyl function and is bonded via the latter to the nitrogen. Such groups are familiar to the skilled worker (Greene, T. W, Protective Groups in Organic Synthesis, J. Wiley & Sons, 1981). He understands thereby for the purposes of the invention in particular a radical selected from the group: formyl, acetyl, propionyl, methoxycarbonyl, ethoxycarbonyl, tert-butoxycarbonyl, Z, Fmoc.

The depicted chemical structures relate to all possible stereoisomers which can be attained by modifying the configuration of the individual chiral centers, axes or planes, that is to say all possible diastereomers, and all optical isomers (enantiomers—R; S compounds) covered thereby or mixtures thereof.

Preparation of N-Boc-L-hydroxyproline

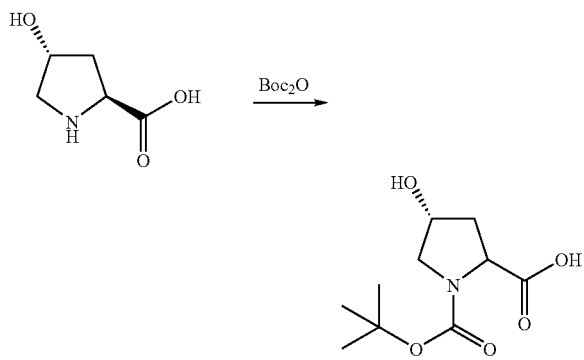

Batch:

| | |
|---|---|
| 132 g (1.00 mol) | of L-hydroxyproline |
| 700 ml | of deionized water |
| 230 g (1.05 mol) | of Boc$_2$O |
| 300 ml | of acetone |

L-Hydroxyproline is dissolved in 700 ml of water at 20-25° C. When the hydroxyproline has dissolved, the pH is adjusted from about 5.5 to 10.5 (10-11) with NaOH (50%). Then, at a temperature of 25-28° C. (max. 30° C.), the Boc$_2$O solution in acetone and the sodium hydroxide solution (50%) are simultaneously metered in so that the temperature is kept between 25-28° C. (max. 30° C.) and the pH at 10.5 (limits 10-11). Duration of addition about 1-2 h.

After the metering is complete, the pH is kept further at 10.5 until constant. An easily stirrable suspension results at the end of the reaction. The total consumption of NaOH (50%) was 174 g (2.18 mol).

The pH is subsequently adjusted to pH 2.6 with HCl (37%). The temperature is always kept at 25° C.; keep it at 25° C. by cooling if it rises a little. CO2 is liberated during the acidification. The evolution of gas starts at a pH of about 7.5 (CO$_2$). Further addition of HCl (37%) should take place sufficiently slowly for the resulting CO$_2$ to be driven out to the same extent. Duration about 30 min in the laboratory. The total amount of HCl (37%) used was: 206 g (2.1 mol).

When the pH of 2.6 (2.5-2.8) is reached, stirring is continued for 15 min in order to stir out residues of dissolved CO$_2$.

Subsequently, 600 ml of MIBK are added, and the mixture is heated to 35-40° C. while stirring (15-20 min). It is subsequently allowed to settle, and the phases are separated.

1st Org. Phase: 920 g

The aqueous phase (about 1 l) is again extracted with 400 ml of MIBK at 35-40° C.

2nd Org. Phase: 360 g

The first organic phase (contains most of the acetone from the reaction) is then distilled under a vacuum down to 200 mbar at a bottom temperature not exceeding 50° C. until almost no further distillate is produced. The 2nd org. phase is added to the distillation bottom, and distillation is continued at 200 mbar.

The vacuum is then slowly lowered further, and distillate is collected.

When about 600 ml have distilled out, the solution is filtered to remove entrained salt (a few g). It is distilled until an approx. 50% strength solution is produced (approx. 400-450 g). Subsequently, 200 ml of MIBK are added and distilled out until the water content in the bottom reaches <0.5 (preferably 0.3%). (Possibly renewed addition of MIBK and distillation).

When the water content of 0.5 is reached, 100-200 ml of MIBK are added and the mixture is cooled to 40° C. 400 ml of hexane are slowly added to the solution at 40° C. During the addition or thereafter, seed crystals are added to the mixture and, after crystallization has started, a further 200 ml of hexane are added.

The suspension is then cooled over the course of 2 h to 15-20 and then with ice/salt further to 0-5° C. And subsequently stirred for 1-2 h. The suspension is filtered and the solid is washed with hexane (2×) 1 l/kg.

258 g of moist product are obtained (heavy crystals). The solid is then dried in vacuo at a max. temperature of 50° C. under 15 mbar. 186 g (80% yield) are obtained.

The final product is checked via HPLC purity (laboratory >98 area %) and NMR (identity), and loss on drying (<0.2%). The product should no longer have an odor of MIBK (prior sample from dryer).

Oxidation of N-Boc-L-hydroxyproline to N-Boc-keto-L-proline

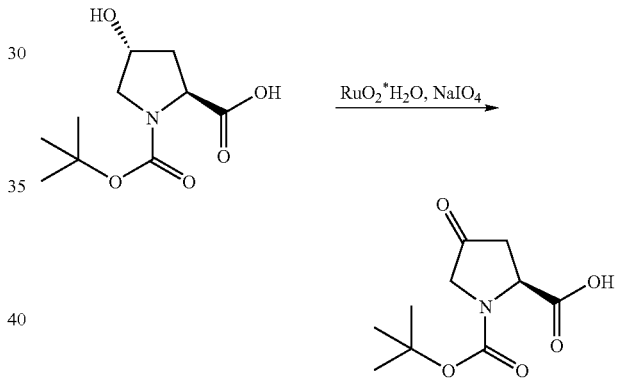

Batch:

| | | |
|---|---|---|
| 50 g (0.22 mol) | of N-Boc-L-hydroxy-proline | |
| 5.5 mg | of RuO$_2$*H$_2$O | Aldrich |
| 69 g (0.322 mol) | of NaIO$_4$ | Fluka |

69 g of sodium (meta)periodate are dissolved in deionized water.

50 g of N-Boc-L-hydroxyproline are dissolved in water. The solution is cooled. Immediately before the reaction, a suspension of 5.5 mg of RuO$_2$*H$_2$O in is added to this solution. Subsequently, the NaIO$_4$ solution is metered in over the course of 1-1.5 h. After metering of 50%, seed crystals are added. The product starts to precipitate out during the addition or thereafter. The reaction mixture is then stirred with further cooling during the after-reaction. The resulting solid is filtered off and washed with 1-2 kg of water/kg of moist product.

38 g of moist product were obtained. These were dried in a water bath at 40° C. (15 mbar) for 3 h. 21 g of dry product were obtained (the crude product is not to be dried in the pilot plant.)

The moist product should be stored in the cool before reprocessing.

(Extrapolated to Total Amount from 20.8 g):

21 g of the dry crude product are suspended in isopropyl acetate (250 ml) and water (55 ml). The product is dissolved by stirring and heating. Then, 1 g of activated carbon (PWA) is added to the two phase mixture, and the mixture is stirred at 35° C. for 30 min. It is subsequently filtered through Celite, and the aqueous phase is removed. The organic phase is distilled in vacuo under 150-170 mbar at a bath temperature of 40-45° C. The product starts to precipitate out even during the distillation. It is distilled until the amount in the bottom is 80 g (about 25 g %). The resulting suspension (heavy crystals) is then cooled to 0° C. over the course of about 2 h, filtered and washed 2× with 20 ml of cold isopropyl acetate each time. 28 g of moist product were obtained and were dried in a water bath at 45° C./15 mbar. 17.0 g of dry product were obtained. Analysis of the final product:

| Identity: | 1H-NMR |
|---|---|
| Purity: | HPLC (>99.5 area %) |
| Optical rotation: | C = 1 in acetone 20° C., |
| Sulfated ash: | <0.2% |

The invention claimed is:

1. A process for preparing N-protected 4-ketoproline compounds of formula (I):

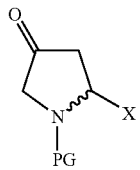

(I)

in which

X is an acid, ester or amide function,

PG is an N-protective group which comprises a carbonyl function and is bonded via this function to the nitrogen, said process comprising oxidizing a 4-hydroxyproline compound with an oxidizing agent in the presence of catalytically active ruthenium compounds, wherein the oxidation is carried out in an aqueous one-phase system, and the oxidation product (I) is induced to crystallize out during the addition of said oxidizing agent.

2. The process of claim 1, wherein said hydroxyproline compound is a compound of formula (III):

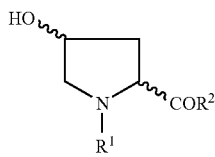

III in which $R^1$ is CO—$R^3$ or fluorenylmethoxycarbonyl, $R^2$ is $NH_2$, or $OR^4$, $R^3$ is (H), ($C_1$-$C_8$)-alkyl, phenyl, benzyl, benzyloxy, $NH_2$, $NO_2$-phenyloxy, $NO_2$-benzyloxy, ($C_1$-$C_8$)-alkoxy or phenyloxy, $R^4$ is H, ($C_1$-$C_8$)-alkyl, benzyl, phenyl, $NO_2$-benzyl, or $NO_2$-phenyl.

3. The process of claim 1, wherein the temperature during the oxidation is kept at ≤30° C.

4. The process of claim 1, wherein the temperature during the oxidation is kept at ≤15° C.

5. The process of claim 1, wherein said oxidizing agent is a hypohalite, halate or perhalate salt.

6. The process of claim 5, wherein said hydroxyproline compound is a compound of formula (III):

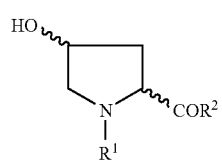

III in which $R^1$ is CO—$R^3$ or fluorenylmethoxycarbonyl, $R^2$ is $NH_2$, or $OR^4$, $R^3$ is (H), ($C_1$-$C_8$)-alkyl, phenyl, benzyl, benzyloxy, $NH_2$, $NO_2$-phenyloxy, $NO_2$-benzyloxy, ($C_1$-$C_8$)-alkoxy or phenyloxy, $R^4$ is H, ($C_1$-$C_8$)-alkyl, benzyl, phenyl, $NO_2$-benzyl, or $NO_2$-phenyl.

7. The process of claim 5, wherein the temperature during the oxidation is kept at ≤30° C.

8. The process of claim 5, wherein the temperature during the oxidation is kept at ≤15° C.

9. The process of claim 1, wherein seed crystals are added to the reaction mixture after addition of 50% of said oxidizing agent.

10. The process of claim 9, wherein said hydroxyproline compound is a compound of formula (III):

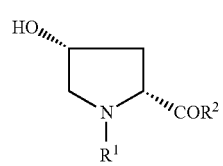

III in which $R^1$ is CO—$R^3$ or fluorenylmethoxycarbonyl, $R^2$ is $NH_2$, or $OR^4$, $R^3$ is (H), ($C_1$-$C_8$)-alkyl, phenyl, benzyl, benzyloxy, $NH_2$, $NO_2$-phenyloxy, $NO_2$-benzyloxy, ($C_1$-$C_8$)-alkoxy or phenyloxy, $R^4$ is H, ($C_1$-$C_8$)-alkyl, benzyl, phenyl, $NO_2$-benzyl, or $NO_2$-phenyl.

11. The process of claim 9, wherein the temperature during the oxidation is kept at ≤30° C.

12. The process of claim 9, wherein the temperature during the oxidation is kept at ≤15° C.

13. The process of claim 9, wherein said oxidizing agent is a hypohalite, halate or perhalate salt.

14. The process of claim 13, wherein the temperature during the oxidation is kept at ≤30° C.

15. The process of claim 13, wherein the temperature during the oxidation is kept at ≤20° C.

16. The process of claim 13, wherein the temperature during the oxidation is kept at ≤15° C.

17. The process of claim 1, wherein said oxidizing agent is sodium periodate and wherein the temperature during the oxidation is kept at ≤30° C.

18. The process of claim 1, wherein the oxidation takes place in a purely aqueous solvent and the temperature during the oxidation is kept at ≤30° C.

19. The process of claim 1, wherein said aqueous solvent also includes a water-soluble organic solvent and the temperature during the oxidation is kept at ≤30° C.

20. The process of claim 19, wherein said oxidizing agent is sodium periodate.

* * * * *